United States Patent [19]

Burke

[11] Patent Number: 4,622,423
[45] Date of Patent: Nov. 11, 1986

[54] HYDROCARBOXYLATION OF BUTADIENE TO 3-PENTENOIC ACID

[75] Inventor: Patrick M. Burke, Wilmington, Del.

[73] Assignee: E. I. Du Pont de Nemours and Company, Wilmington, Del.

[21] Appl. No.: 669,851

[22] Filed: Nov. 9, 1984

[51] Int. Cl.$^4$ .................. C07C 51/14; C07C 57/03
[52] U.S. Cl. ................................................ 562/522
[58] Field of Search ....................................... 562/522

[56] References Cited

U.S. PATENT DOCUMENTS

| | | | |
|---|---|---|---|
| 2,586,341 | 2/1952 | Hyson | 562/522 |
| 3,579,552 | 5/1971 | Craddock | 260/413 |
| 3,876,695 | 4/1975 | Kutepow | 562/522 |
| 4,172,087 | 10/1979 | Knifton | 260/410.6 |

FOREIGN PATENT DOCUMENTS

| | | |
|---|---|---|
| 0075524 | 3/1983 | European Pat. Off. . |
| 3040432 | 12/1982 | Fed. Rep. of Germany . |
| 1092694 | 2/1965 | United Kingdom . |

OTHER PUBLICATIONS

Imyanitov et al., Karbonilirovonie Nenasyshchennykh Uglevodorodov (1968) 225–32, CA 71 216484.

Mechanistic Pathways in the Catalysis of Olefin Hydrocarboxylation by Rhodium, Iridium, and Cobalt Complexes, D. Forster et al., Catal. Rev.–Sci. Eng. 23(1&2) pp. 89–105 (1981).

Primary Examiner—Werren B. Lone

[57] ABSTRACT

The preparation of 3-pentenoic acid by hydrocarboxylating butadiene with carbon monoxide and water in the presence of a rhodium-containing catalyst, an iodide promoter and certain inert halocarbon solvents, e.g., methylene chloride.

5 Claims, No Drawings

HYDROCARBOXYLATION OF BUTADIENE TO 3-PENTENOIC ACID

BACKGROUND OF THE INVENTION

1. Field of the Invention

The present invention relates to the preparation of 3-pentenoic acid by hydrocarboxylating butadiene with carbon monoxide and water in the presence of a rhodium-containing catalyst, an iodide promoter and certain inert halocarbon solvents, e.g., methylene chloride.

2. Description of the Prior Art

U.S. Pat. No. 3,876,695, issued on Apr. 8, 1975 to Nicholaus Von Kutepow, discloses a process for the production of adipic acid by the reaction of butadiene, carbon monoxide and water using certain rhodium carbonyl complexes along with free or combined halogen as a catalyst system. The patentee discloses the advantage of using a solvent in the system which is a nonsolvent for adipic acid and cite as operable aromatic hydrocarbons, e.g., xylene, saturated cycloaliphatic hydrocarbons, e.g., cyclohexane and saturated aliphatic hydrocarbons, preferably those having 8-12 carbon atoms. The patentee suggests introducing catalyst in aqueous solution when practicing the process continuously. In Column 1, lines 10-50, the patentee discusses representative art on the preparation of acids and esters via carbonylation.

U.S. Pat. No. 4,172,087, issued on Oct. 23, 1979 to J. F. Knifton discloses a process for the carbonylation and concurrent dimerization of olefins such as 1,3-butadiene in the presence of hydroxylated coreactants, a dual function palladium catalyst and a tertiary nitrogen-containing base to produce acids and ester derivatives of unsaturated carboxylic acids. The reaction of butadiene is taught to produce 3-pentenoic acid and 3,8-nonadienoic acid and their corresponding ester derivatives. The patentees do not discuss the desirability and/or effect of conducting the reaction in the presence of a solvent. The catalyst system requires the presence of ligands of Group VB elements to stabilize the palladium salts. Included in these ligands are numerous phosphorus-containing compounds, e.g., bis(1,2-diphenylphosphino)ethane.

European Pat. No. 0075524, published on Mar. 30, 1983 and assigned to Rhone-Poulenc Chimie De Base, discloses a process for the preparation of beta, gamma unsaturated carboxylic acids by the carbonylation of conjugated dienes using a palladium catalyst with a halide promoter to produce the corresponding esters.

The production of 3-pentenoic acid is discussed in an article by Imyanitov et al., Karbonilirovonie Nenasyshchennykh Uglevodorodov (1968) 225-32, CA 71 216484, a portion of which disclosure appears in U.K. Pat. No. 1,092,694 published on Feb. 4, 1965. The reaction was studied in a pyridine solvent with cobalt carbonyl catalysts under a pressure of 120-500 atmospheres. The authors note that the order with respect to water changes from approximately zero where the reaction mixture comprises equal molar amounts of water to −1 at a 13-fold excess of water. The preparation of the esters of 3-pentenoic acid using cobalt catalysts is disclosed in German Patent DE No. 3040432, published on June 19, 1981. Hydrocarboxylations employing rhodium catalysts are discussed in the article *Mechanistic Pathways in the Catalysis of Olefin Hydrocarboxylation by Rhodium, Iridium, and Cobalt Complexes*, D. Forster et al., Catal. Rev. - Sci, Eng. 23(1&2) p 89-105 (1981).

U.S. Pat. No. 3,579,552 discloses the use of rhodium catalyst with an iodide promoter to prepare carboxylic acids from olefins and other ethylenically unsaturated compounds. In Column 8, lines 31-42, the patentees disclose that an excess of water is beneficial to the reaction which, according to the teachings of the patent, is conducted using the olefins themselves or carboxylic acids as solvent. Example 9 demonstrates the employment of acetic acid as a solvent for the reaction of butadiene. In all cases a significant percentage of the products are branched.

SUMMARY OF THE INVENTION

The present invention is a process for the preparation of 3-pentenoic acid by the reaction of butadiene, carbon monoxide and water in the presence of a rhodium-containing catalyst, an iodide promoter and certain halocarbon solvents having 1-2 carbon atoms, e.g., methylene chloride, at a temperature in the range 100°-220° C. and a pressure in the range 20-200 atm. The amount of water in the reaction medium is maintained at less than about 4.5% and preferably less than 3.5% by weight based upon the weight of the reaction medium in order to maintain catalyst activity and to assure a high yield.

DETAILED DESCRIPTION OF THE INVENTION

In the hydrocarboxylation of olefins emphasis has been placed upon the production of adipic acid and the adipate ester directly from butadiene because these compounds are intermediates for nylon polymers.

It has been found that the yield to the desired linear end-products, e.g., adipic acid, can be improved if the reaction is conducted in two steps. In the first step 3-pentenoic acid is produced which is then hydrocarboxylated in a second step to adipic acid. This application is directed to the first step, i.e., the production of 3-pentenoic acid in exceptionally high yields and under relatively mild conditions. In addition, it should be noted that the selectivity to the linear 3-pentenoic acid is quite high in the process of the present invention, in most cases exceeding 95-97% with the principal carbonylated byproduct being 2-methyl-3-butenoic acid.

The source of the reactants for the present process is not particularly critical. Commercially available grades of carbon monoxide and butadiene are quite satisfactory.

The reaction can be conducted over a reasonably wide temperature range, but relatively mild conditions are preferred. Acceptable yield is realized at temperatures in the range 100°-220° C. and preferably 100°-160° C. Temperatures above the upper end of the range result in a significant reduction in the conversion of butadiene to 3-pentenoic acid. At temperatures below the lower end of the range, the reaction is too slow to be economic.

Relatively moderate pressures, i.e., in the range 20-200 and preferably 25-75 atm are satisfactory. The partial pressure of carbon monoxide is usually maintained in the range 10-200 atm and preferably 13-70 atm.

The catalyst precursor employed can be any rhodium complex that is free of interferring ligands particularly bidentate phosphine and nitrogen ligands. Rhodium complexes such as rhodium(III) chloride-$RhCl_3 \cdot 3H_2O$, rhodium(III) iodide-$RhI_3$, rhodium carbonyliodide- Rh(CO)$_n$I$_3$ (N=2-3), rhodium(III) nitrate-Rh(NO$_3$)$_3$.2-H$_2$O, dodecacarbonyltetrarhodium(O)-Rh$_4$(CO)$_{12}$, acetylacetonatodicarbonylrhodium(I)-Rh(CO)$_2$(C$_5$H$_7$O$_2$), chlorobis(ethylene)rhodium(I) dimer-[Rh(C$_2$H$_4$)$_2$Cl]$_2$, acetylacetonato(1,5-cyclooctadiene)rhodium(I)-Rh(C$_8$H$_{12}$)(C$_5$H$_7$O$_2$), chlorocarbonylbis(triphenylphosphine) rhodium(I)-RhCl(CO)(PPh$_3$)$_2$, hexadecacarbonylhexarhodium-(O)-Rh$_6$(CO)$_{16}$, tris(acetylacetonato)rhodium(III)-Rh(C$_5$H$_7$O$_2$)$_3$, rhodium(II)octonoate dimer-Rh2[CO$_2$(CH$_2$)$_6$ CH$_3$]$_4$, chlorodicarbonylrhodium(I) dimer-[Rh(CO)$_2$Cl]$_2$, chloro(1,5-cyclooctadiene)rhodium(I) dimer-[Rh(C$_8$H$_{12}$)Cl]$_2$, acetylacetonatobis(ethylene)rhodium(I)-Rh(C$_2$H$_4$)$_2$(C$_5$H$_7$O$_2$) and rhodium(II)acetate dimer-Rh$_2$(CO$_2$CH$_3$)$_4$.

The concentration of catalyst precursor is not critical but is usually maintained in the range 0.04-0.16% by weight of rhodium metal based upon the weight of the reaction medium. The catalyst, which can be performed or can be formed in situ, must be promoted, preferably by iodide, to achieve a satisfactory reaction rate. Hydrogen iodide is the preferred iodide source, but an alkyl iodide having 1-10 carbon atoms, e.g., methyl iodide, is a suitable promoter especially at the higher reaction temperature. Other suitable promoters include iodoethane, 1-iodobutane, 2-iodopropane, 1-iodopropane and iodoheptane. As believed apparent from the foregoing, the promoter and rhodium can be present in the same compound as in rhodium iodide. Generally the concentration of promoter is between 0.1-1.0% by weight iodide based upon the weight of the reaction medium and at a mole ratio to rhodium of at least 3.0/1.

The reaction is carried out in the presence of a solvent the selection of which is critical to the present invention. The coordinating solvents, e.g., pyridine, dimethylformamide and dimethylsulfoxide and N-methylpyrrolidone block the active cities on the rhodium and should be avoided. Solvents such as acetic acid in aqueous solution are also undesirable. Nonpolar solvents such as cyclohexane and toluene are undesirable because they promote the shift reaction resulting in the reduction of butadiene to butene. Generally the solvent should be essentially inert to the reactants and should resist hydrolysis. The preferred solvents include saturated halocarbon solvents having 1-2 carbon atoms, e.g., methylene chloride, 1,1,2,2-tetrachloroethane, 1,1,2-trichloroethane, 1,1-dichloroethane, chloroform and carbon tetrachloride. Methylene chloride is preferred. Unsaturated halocarbon solvents such as tetrachloroethylene result in very low yields to 3-pentenoic acid, although butadiene consumption is quite high. The amount of solvent employed can vary widely, e.g., 50-99, usually 80-99 and preferably 85-95% by weight based upon the weight of the reaction mixture.

The amount of water in the reaction medium is critical to the present invention and must not exceed 4.5% by weight based upon the weight of the solvent. Preferably the water level is maintained at less than 3.5% on the same basis. The reaction can be carried out batchwise or continuously.

The following examples are presented to illustrate but not to restrict the present invention. Parts and percentages are by weight unless otherwise noted.

EXAMPLE 1

A 300 ml mechanically stirred reactor constructed of Hastelloy-C was flushed with nitrogen followed by high purity carbon monoxide and then charged with 130 ml of methylene chloride containing 0.37 g of chloro(1,5-cyclooctodiene)rhodium(I) dimer. The reactor was closed, and a solution of 14.2 g butadiene containing 10 g dodecane (as an internal standard) and 10 mg of 2,6-di-t-butyl-4methylphenol (polymerization inhibitor) and 10 ml methylene chloride at a pressure of 5.4 atm was injected into the reactor. After the introduction of the butadiene, the pressure in the reactor was increased to 400 psi with carbon monoxide and then heated until the temperature of the contents reached 140° C. whereupon a solution of 0.57 g of hydrogen iodide in 5.43 g of water was injected into the reactor. After this injection was complete, the pressure of the reactor was increased to 47.6 atm with carbon monoxide and maintained at that pressure and a temperature of 140° C. during the hydrocarboxylation. After approximately 8 minutes, the consumption of carbon monoxide began and was monitored by measuring the pressure drop in a reservoir cylinder. The reaction was terminated after five hours when the uptake of carbon monoxide ceased, corresponding to a consumption of approximately 84.7% of the theoretical amount of carbon monoxide. The contents of the reactor were recovered by cooling the reactor to approximately 20° C. and slowly venting the reactor to the atmosphere. The reactor contents were removed and the reactor was washed first with 200 ml of tetrahydrofuran heated to 110° C. and second with 150 ml of tetrahydrofuran at room temperature. The wash liquids and reactor contents were combined and analyzed. A 79.0% conversion to 3-pentenoic acid and less than 0.5% of 2-methyl-3-butenoic acid based upon the butadiene charged was obtained. Based upon a conversion (84.7%) calculated from carbon monoxide consumption, the yield of 3-pentenoic acid was 93.3%. Analysis also indicated minor amounts of adipic acid (1.49% conversion) and alpha-methylglutaric acid (1.30% conversion). The analysis of the vapor space in the reactor showed an initial concentration of 7.43 volume percent butadiene and a final concentration of 1.45% along with the formation of 0.11% 1-butene, 0.27% 2-butene and 2.1% carbon dioxide. The results correspond to a reduction of butadiene to butene of approximately 5.6%. No other products were detected in the gas or liquid phase analysis. The general results are reported in the Table.

EXAMPLES 2-7

Example 1 was repeated except that the amount of butadiene was reduced and the temperature and pressure varied as indicated in the Table.

EXAMPLES 8-11

Example 1 was repeated except that the amount of water introduced with the hydrogen iodide promoter was varied as set forth in the Table.

EXAMPLE 12

Example 1 was repeated except 1,1,2,2-tetrachloroethane was substituted for methylene chloride. The results are reported in the Table.

EXAMPLES 13-15

Example 1 was repeated except that the indicated catalyst precursors were used instead of the catalyst precursor-chloro(1,5-cyclooctodiene)rhodium(I) dimer. The results are reported in the Table.

| Example No. | Catalyst Precursor |
| --- | --- |
| 13 | methoxy(1,5-cyclooctadiene)rhodium(I) dimer-[Rh(COD)OMe]$_2$ |
| 14 | hexarhodium hexadecacarbonyl-Rh$_6$(CO)$_{16}$ |
| 15 | chlorocarbonylbis(triphenylphosphine)-rhodium(I)-RhCl(CO)(PPh$_3$)$_2$ | in 6.0 ml water. Uptake of carbon monoxide was slower than in Example 16. About 3.5 hours were required for the carbon monoxide uptake to reach 50% of the theoretical value. The reaction was terminated after carbon monoxide uptake ceased. The products were recovered as described in Example 1. The results are summarized in the Table.

TABLE

| Ex. No. | Temp. °C. | Total Pressure (atms) | Water[b] (wt %) | Butadiene Introduced (gram) | Conversion[a] (%) | | Vapor Above Reaction at Termination (% by volume) | |
| --- | --- | --- | --- | --- | --- | --- | --- | --- |
| | | | | | 3-pentenoic Acid | Diacids | Butenes[c] | Carbon Dioxide |
| 1  | 140 | 47.6 | 2.9 | 14.2 | 79.0 | 2.8 | 5.6 | 2.1 |
| 2  | "   | "    | 1.4 | 8.3  | 64.7 | 0.9 | 3.7 | 1.0 |
| 3  | "   | 68.0 | "   | 7.9  | 80.1 | 2.1 | 2.1 | 0.5 |
| 4  | "   | 27   | "   | 8.6  | 58.7 | 8.6 | 3.9 | 2.6 |
| 5  | "   | 20.4 | "   | 8.1  | 34.0 | 5.7 | 9.9 | 2.9 |
| 6  | 100 | 47.6 | "   | 8.8  | 54.6 | 0   | 1.8 | 0.3 |
| 7  | 160 | "    | "   | 8.0  | 56.3 | 4.5 | 3.1 | —  |
| 8  | 140 | "    | "   | 8.3  | 65.2 | 0   | 3.5 | 0.5 |
| 9  | "   | "    | 1.8 | 8.4  | 63.4 | 7.0 | 6.8 | 1.6 |
| 10 | "   | "    | 4.2 | 8.1  | 38.8 | 0   | 5.4 | 1.1 |
| 11 | "   | "    | 5.5[d] | 28.4 | 67.4 | 1.4 | 4.0 | 2.1 |
| 12 | "   | "    | 1.4 | 8.1  | 57.8 | 5.7 | 3.4 | 1.2 |
| 13 | "   | "    | "   | 8.2  | 63.5 | 0   | 3.1 | 3.1 |
| 14 | "   | "    | "   | 8.1  | 55.0 | 0   | 3.3 | 3.3 |
| 15 | "   | "    | "   | 8.1  | 51.7 | 0   | 12.1| 2.3 |
| 16 | "   | "    | 3.0 | 8.3  | 71.6 | 2.5 | 2.0 | 2.0 |
| 17 | "   | "    | 3.0 | 8.4  | 54.6 | 1.5 | 1.8 | 1.8 |

[a]Number of moles of product produced per mole of butadiene added X100.
[b]Based upon weight of solvent.
[c]Percentage of the initial volume percent butadiene.
[d]Approximately 40% added at an initiation of the reaction remainder added at a constant rate over a two-hour period.

EXAMPLE 16

The procedure in Example 1 was modified as follows to use a methyl iodide promoter. The reactor was charged with 4.26 g methyl iodide, 10 g dodecane (internal GC standard), 8.3 g butadiene, 6.0 g water and 140 ml methylene chloride solvent. The reactor was pressurized with 48 atm carbon monoxide and heated to 140° C. as described previously. The reaction was initiated by adding a solution of 0.37 g chloro(1,5-cyclooctadiene)rhodium(I) dimer in 10 ml methylene chloride. After approximately two hours, the consumption of carbon monoxide began. The reaction was terminated after five hours. The products were recovered as described in Example 1 and the results are summarized in the Table.

Example 17

Example 16 was repeated except that the reaction was initiated by adding a solution of 0.4 g RhCl$_3$.3H$_2$O

I claim:

1. A process for the preparation of 3-pentenoic acid which comprises reacting in methylene chloride solvent, butadiene with carbon monoxide and water in the presence of a rhodium-containing catalyst and an iodide promoter at a temperature in the range 100°–220° C. and a pressure in the range 20–200 atm while maintaining the amount of water less than about 4.5% by weight based upon the weight of the solvent.

2. The process of claim 1 wherein the water is maintained at less than about 3.5%.

3. The process of claim 1 wherein the iodide compound is hydrogen iodide.

4. The process of claim 2 wherein the temperature is maintained in the range 100°–160° C. and the pressure is maintained in the range 25–75 atm.

5. The process of claim 3 wherein the temperature is maintainied in the range 100°–160° C. and the partial pressure of carbon monoxide is maintained in the range 13–70 atm.

* * * * *